(12) United States Patent
Suzuki

(10) Patent No.: US 11,826,530 B2
(45) Date of Patent: Nov. 28, 2023

(54) BALLOON CATHETER AND METHOD OF MANUFACTURING BALLOON CATHETER

(71) Applicant: TERUMO KABUSHIKI KAISHA, Tokyo (JP)

(72) Inventor: Kenta Suzuki, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1029 days.

(21) Appl. No.: 16/672,734

(22) Filed: Nov. 4, 2019

(65) Prior Publication Data

US 2020/0061352 A1 Feb. 27, 2020

Related U.S. Application Data

(63) Continuation of application No. PCT/JP2018/018510, filed on May 14, 2018.

(30) Foreign Application Priority Data

May 15, 2017 (JP) ................................. 2017-096740

(51) Int. Cl.
A61M 25/10 (2013.01)

(52) U.S. Cl.
CPC ..... *A61M 25/1036* (2013.01); *A61M 25/1034* (2013.01); *A61M 2025/1043* (2013.01); *A61M 2205/02* (2013.01); *A61M 2207/00* (2013.01)

(58) Field of Classification Search
CPC .......... A61M 25/1036; A61M 25/1034; A61M 25/104; A61M 2025/1043;
(Continued)

(56) References Cited

U.S. PATENT DOCUMENTS 6,706,010 B1 * 3/2004 Miki ................. A61M 25/1036
604/103
6,827,798 B1 12/2004 Ichikawa et al.
(Continued)

FOREIGN PATENT DOCUMENTS

CN 103118734 A * 5/2013 ........ A61M 25/0009
JP 2001149480 A 6/2001
(Continued)

OTHER PUBLICATIONS

"Nylon-12." Wikipedia. <https://en.wikipedia.org/wiki/Nylon_12>. Accessed Feb. 27, 2023. (Year: 2023).*
(Continued)

*Primary Examiner* — Scott J Medway
(74) *Attorney, Agent, or Firm* — BUCHANAN INGERSOLL & ROONEY PC

(57) ABSTRACT

A balloon catheter is disclosed which allows easier fusion-bonding between an inner tube shaft and an outer tube shaft and in which the inner tube shaft can be prevented from being warped when the inner tube shaft passes through a stenosed site, and a method of manufacturing such a balloon catheter. The balloon catheter includes an inner tube shaft having a first layer and a second layer located on an inner surface side of the first layer. The outer tube shaft is fusion-bonded to the first layer and recessed toward the inner tube shaft side. The first layer is formed of a material having higher optical absorption property than the outer tube shaft and the second layer. The second layer is formed of a material having a melting point higher than that of the first layer.

14 Claims, 5 Drawing Sheets

(58) Field of Classification Search
CPC .......... A61M 2205/02; A61M 2207/00; A61M 25/0045; A61M 25/10; A61M 25/1027; B29C 66/723; B29C 65/1677; B29C 66/71
See application file for complete search history.

(56) References Cited

U.S. PATENT DOCUMENTS

| | | | | |
|---|---|---|---|---|
| 9,433,760 | B2* | 9/2016 | Subramaniam | A61B 18/00 |
| 9,931,491 | B2* | 4/2018 | Shimogami | A61M 25/0052 |
| 2003/0125710 | A1* | 7/2003 | Pepin | A61M 25/0045 604/525 |
| 2004/0186506 | A1* | 9/2004 | Simpson | A61M 25/0009 606/194 |
| 2007/0060910 | A1* | 3/2007 | Grandt | A61M 25/0032 604/524 |
| 2007/0078439 | A1* | 4/2007 | Grandt | B23K 26/009 604/523 |
| 2009/0162531 | A1* | 6/2009 | Nesbitt | A61L 29/18 427/2.12 |
| 2011/0245807 | A1* | 10/2011 | Sakata | A61M 25/005 604/526 |
| 2012/0197237 | A1* | 8/2012 | Holzbauer | A61M 25/0045 604/540 |

FOREIGN PATENT DOCUMENTS

| | | |
|---|---|---|
| JP | 2001191412 A | 7/2001 |
| JP | 2004216175 A | 8/2004 |
| JP | 2006158766 A | 6/2006 |
| WO | 2014/156600 A1 | 10/2014 |

OTHER PUBLICATIONS

"Polytetrafluoroethylene." Wikipedia. <https://en.wikipedia.org/wiki/Polytetrafluoroethylene>. Accessed Feb. 27, 2023. (Year: 2023).*

The extended European Search Report dated Jan. 27, 2021, by the European Patent Office in corresponding European Patent Application No. 18801402.1-1132. (8 pages).

International Search Report (with English Translation) and Written Opinion issued in corresponding International Patent Application No. PCT/JP2018/018510, 7 pages (dated Jul. 20, 2018).

An English Translation of the International Search Report (Form PCT/ISA/210) and the Written Opinion of the International Searching Authority (Form PCT/ISA/237) dated Jul. 10, 2018, by the Japanese Patent Office in corresponding International Application No. PCT/JP2018/018510. (6 pages).

* cited by examiner

BALLOON CATHETER AND METHOD OF MANUFACTURING BALLOON CATHETER

CROSS-REFERENCES TO RELATED APPLICATIONS

This application is a continuation of International Application No. PCT/JP2018/018510 filed on May 14, 2018, which claims priority to Japanese Application No. 2017-096740 filed on May 15, 2017, the entire content of both of which is incorporated herein by reference.

FIELD OF THE DISCLOSURE

The present disclosure generally relates to a balloon catheter and a method of manufacturing a balloon catheter.

BACKGROUND ART

Balloon catheters are medical devices that can dilate a lesion area such as a stenosed site formed in a biological lumen such as a blood vessel.

A balloon catheter can include an inner tube shaft provided with a lumen forming a guide wire lumen, an outer tube shaft provided with a lumen (inflation lumen) for circulating a pressurizing medium (i.e., a liquid), and a balloon fixed to the inner tube shaft and the outer tube shaft. In the balloon catheter configured in this way, the inner tube shaft is located coaxially with the outer tube shaft, in a state where a distal end of the inner tube shaft is inserted into the lumen of the outer tube shaft so that the inner tube shaft protrudes from a distal side of the outer tube shaft.

When an operator causes the balloon catheter to pass through the lesion area such as the stenosed site in a medical procedure using the balloon catheter, in some cases, the operator may perform a thrust operation on the balloon catheter from a proximal side. For example, if the above-described thrust operation is performed on the balloon catheter in a state where a distal end of the balloon catheter bumps against the stenosed site, the inner tube shaft receives a reaction force responded to the thrust operation. In this manner, the inner tube shaft cannot move in a state where the inner tube shaft is parallel to the outer tube shaft while keeping coaxial with the outer tube shaft. Consequently, the inner tube shaft may be warped in some cases. If the inner tube shaft is warped in the balloon catheter, a balloon fixed to the inner tube shaft may buckle. In addition, since the inner tube shaft is warped, the balloon catheter may have poor pushing ability (pushing performance).

For example, with regard to the problem as described above, JP-A-2001-149480 below has proposed the balloon catheter as follows. An outer surface of the inner tube shaft and an inner surface of the outer tube shaft can be fusion-bonded to each other at a position separated to the proximal side from the balloon. In addition, JP-A-2001-149480 discloses a method of fusion-bonding the outer surface of the inner tube shaft and the inner surface of the outer tube shaft to each other by an ultrasound fusion-bonding method, in which ultrasound waves are emitted from an ultrasound oscillation horn being pressed against the outer surface of the outer tube shaft.

As described above, according to the balloon catheter disclosed in JP-A-2001-149480, the outer surface of the inner tube shaft and the inner surface of the outer tube shaft can be partially fusion-bonded to each other. In this manner, even in a case of performing the thrust operation in a state where the distal end of the balloon catheter bumps against the stenosed site, the inner tube shaft can move in the state where the inner tube shaft is parallel to the outer tube shaft while keeping coaxial with the outer tube shaft.

In addition, according to a method of manufacturing the balloon catheter disclosed in JP-A-2001-149480, an ultrasound fusion-bonding method is adopted as a method of fusion-bonding the outer surface of the inner tube shaft and the inner surface of the outer tube shaft to each other. In this manner, when fusion-bonding is carried out, portions other than a joint portion can be prevented from being affected by heat.

According to the above manufacturing method, a worker who carries out manufacturing work adjusts an output of the ultrasound waves oscillating from the ultrasound oscillation horn. In this manner, the worker can help prevent the portions other than the joint portion from being affected by the heat.

However, in a case where the inner tube shaft and the outer tube shaft are fusion-bonded to each other by means of ultrasound fusion-bonding, the heat quantity of fusion-bonding contributing to the fusion-bonding between the inner tube shaft and the outer tube shaft depends on a force that brings the inner tube shaft and the outer tube shaft into contact with each other or frictional resistance acting between the inner tube shaft and the outer tube shaft. Therefore, the ultrasound fusion-bonding between the inner tube shaft and the outer tube shaft can vary depending on a contact state between the inner tube shaft and the outer tube shaft or each material of the inner tube shaft and the outer tube shaft.

Therefore, in a case of adopting the ultrasound fusion-bonding method using the ultrasound oscillation horn, the worker needs to consider the material in view of the frictional resistance between the inner tube shaft and the outer tube shaft. In addition, when the worker joins the inner tube shaft and the outer tube shaft to each other, while the worker can accurately adjust the contact state between the respective shafts, the worker has to precisely control an output of the ultrasound waves oscillating from the ultrasound oscillation horn, and a force or a position for pressing the ultrasound oscillation horn against the outer surface of the outer tube shaft. Therefore, depending on a shape or a material of the inner tube shaft or the outer tube shaft, the ultrasound fusion-bonding may be less useful in some cases.

SUMMARY

A balloon catheter is disclosed which allows easier fusion-bonding between an inner tube shaft and an outer tube shaft and in which the inner tube shaft can be prevented from being warped when the inner tube shaft passes through a stenosed site, and a method of manufacturing such a balloon catheter.

A balloon catheter is disclosed, which includes an outer tube shaft having a lumen, an inner tube shaft located in the lumen of the outer tube shaft, and a balloon fixed to a distal side of the inner tube shaft and a distal side of the outer tube shaft. The inner tube shaft has a first layer and a second layer located on an inner surface side of the first layer. The outer tube shaft is fusion-bonded to the first layer and recessed toward the inner tube shaft side. The first layer is formed of a material having an optical absorption property greater than the outer tube shaft and the second layer. The second layer is formed of a material having a melting point greater than that of the first layer.

In addition, a method is disclosed of manufacturing a balloon catheter. The manufacturing method can include supplying an outer tube shaft, an inner tube shaft, and a balloon to be fixed to a distal side of the inner tube shaft and a distal side of the outer tube shaft, the inner tube shaft having a first layer and a second layer located on an inner surface side of the first layer, the first layer being formed of a material having an optical absorption property greater than the outer tube shaft and the second layer, and the second layer being formed of a material having a melting point greater than that of the first layer, locating the inner tube shaft so that a distal portion of the inner tube shaft protrudes from a distal end of the outer tube shaft and fixing the balloon to the distal side of the inner tube shaft and the distal side of the outer tube shaft, applying heat generating light from an outer surface side of the outer tube shaft to a contact location between the inner tube shaft and the outer tube shaft in a state where a portion of an outer surface of the inner tube shaft is brought into contact with an inner surface of the outer tube shaft, and melting the first layer by causing a portion of the first layer to absorb the heat generating light so as to generate heat and fusion-bonding the outer tube shaft and the inner tube shaft to each other.

In manufacturing the balloon catheter configured as described above, the heat generating light is applied from the outer surface side of the outer tube shaft. In this manner, the heat generating light is absorbed by the first layer of the inner tube shaft having an optical absorption property greater than the outer tube shaft and the second layer of the inner tube shaft. In this manner, the first layer of the inner tube shaft is melted, and the inner tube shaft and the outer tube shaft are fusion-bonded to each other. Then, when the inner tube shaft and the outer tube shaft are fusion-bonded, the outer surface of the outer tube shaft and the inner surface of the inner tube shaft are less likely to be thermally affected by heat generation of the first layer. Accordingly, sliding ability of a guide wire passing through the lumen of the inner tube shaft can be prevented from being degraded, or a leakage can be prevented from occurring in the lumen of the outer tube shaft.

According to the method of manufacturing the balloon catheter, when the outer tube shaft and the inner tube shaft are fusion-bonded to each other, the heat generating light is applied from the outer surface side of the outer tube shaft. The heat generating light is absorbed in the contact location between the inner surface of the outer tube shaft and the outer surface of the inner tube shaft. If the heat generating light is absorbed, the first layer of the inner tube shaft is melted, thereby fusion-bonding the inner tube shaft and the outer tube shaft to each other. Therefore, a worker who manufactures the balloon catheter carries out relatively easy work for applying the heat generating light toward the outer tube shaft and the inner tube shaft. In this manner, while the outer surface of the outer tube shaft and the inner surface of the inner tube shaft are prevented from being excessively affected by the heat generation, the inner tube shaft and the outer tube shaft can be fusion-bonded to each other.

In accordance with an aspect, a balloon catheter is disclosed comprising: an outer tube shaft having a lumen; an inner tube shaft located in the lumen of the outer tube shaft, the inner tube shaft having a first layer and a second layer located on an inner surface side of the first layer; a balloon fixed to a distal side of the inner tube shaft and a distal side of the outer tube shaft, and the outer tube shaft being recessed toward the inner tube shaft side; and wherein a material of the first layer has an optical absorption property greater than an optical absorption property of the material of the outer tube shaft and an optical absorption property of a material of the second layer, and a melting point of the material of the second layer is greater than a melting point of the material of the first layer.

In accordance with another aspect, a balloon catheter is disclosed comprising: an outer tube shaft having a lumen; an inner tube shaft located in the lumen of the outer tube shaft, the inner tube shaft having a first layer, a second layer located on an inner surface side of the first layer, and a third layer interposed between the first layer and the second layer; a balloon fixed to a distal side of the inner tube shaft and a distal side of the outer tube shaft, and the outer tube shaft being recessed toward the inner tube shaft side; a material of the first layer having an optical absorption property greater than an optical absorption property of the material of the outer tube shaft and an optical absorption property of a material of the second layer, and a melting point of the material of the second layer is at least 10° C. greater than a melting point of the material of the first layer; and wherein a material of the third layer has a greater affinity for the material of the second layer than the material of the first layer.

In accordance with an aspect, a method is disclosed of manufacturing a balloon catheter, comprising: supplying an outer tube shaft, an inner tube shaft, and a balloon configured to be fixed to a distal side of the inner tube shaft and a distal side of the outer tube shaft, the inner tube shaft having a first layer and a second layer located on an inner surface side of the first layer, an optical absorption property of a material of the first layer being greater than an optical absorption property of a material of the outer tube shaft and an optical absorption property of a material of the second layer, and a melting point of the material of the second layer being greater than a melting point of the material of the first layer; locating the inner tube shaft so that a distal portion of the inner tube shaft protrudes from a distal end of the outer tube shaft and fixing the balloon to the distal side of the inner tube shaft and the distal side of the outer tube shaft; applying heat generating light from an outer surface side of the outer tube shaft to a contact location between the inner tube shaft and the outer tube shaft in a state where a portion of an outer surface of the inner tube shaft is brought into contact with an inner surface of the outer tube shaft; and melting the first layer by causing a portion of the first layer to absorb the heat generating light to generate heat and fusion-bonding the outer tube shaft and the inner tube shaft to each other.

DESCRIPTION OF EMBODIMENTS

Set forth below with reference to the accompanying drawings is a detailed description of embodiments of a balloon catheter and a method of manufacturing a balloon catheter representing examples of the inventive balloon catheter and method of manufacturing a balloon catheter disclosed here. The dimensions or scales on the drawings may be exaggerated or different from actuality/reality for convenience of description and illustration.

Figure 1:
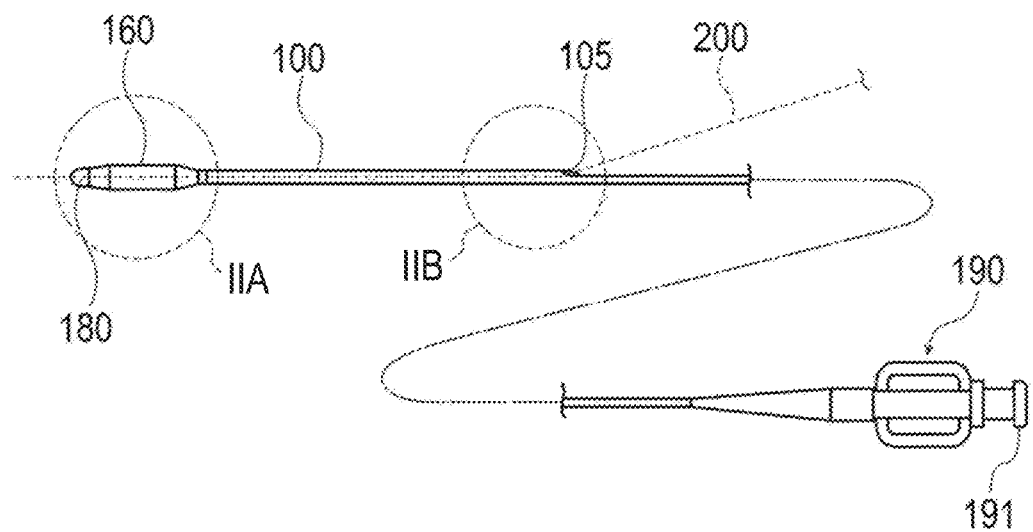
FIG. 1 is a view illustrating a balloon catheter according to an embodiment.

As illustrated in FIG. 1, a balloon catheter 10 according to the present embodiment can be a medical device that widens and treats a lesion area by inflating a balloon 160 located on a distal side of a shaft 100 in the lesion area such as a stenosed site formed in a biological lumen.

In accordance with an exemplary embodiment, the balloon catheter 10 can be a balloon catheter for PTCA treatment used in order to widen the stenosed site of a coronary artery. However, for example, the balloon catheter 10 can be a balloon catheter in order to treat the lesion area such as the stenosed site formed in a biological organ such other blood vessels, a bile duct, a trachea, an esophagus, the other digestive tract, a urethra, an aurinasal lumen, and other organs.

Hereinafter, the balloon catheter 10 will be described.

As illustrated in FIG. 1, the balloon catheter 10 has an elongated shaft 100, the balloon 160 located on the distal side of the shaft 100, and a hub 190 located on a proximal side of the shaft 100.

In the description of the embodiment, a side on which the balloon 160 is located will be referred to as a distal side of the balloon catheter 10, a side on which the hub 190 is located will be referred to as a proximal side of the balloon catheter 10, and a direction in which the shaft 100 extends will be referred to as an axial direction.

As illustrated in FIG. 1, the balloon catheter 10 can be configured as a so-called rapid exchange type catheter in which a proximal opening portion (guide wire port) 105 allowing a guide wire 200 to be insertable and removable is formed close to a distal portion side of the shaft 100.

Figure 2A:
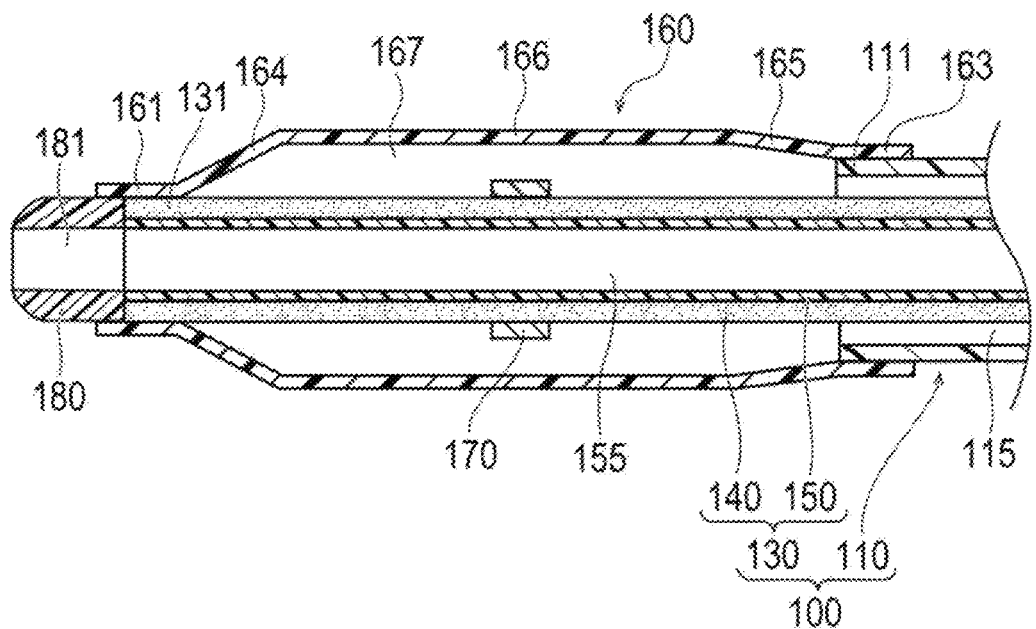
FIG. 2A is an enlarged sectional view of a portion surrounded by a broken line portion IIA in FIG. 1.
Figure 2B:
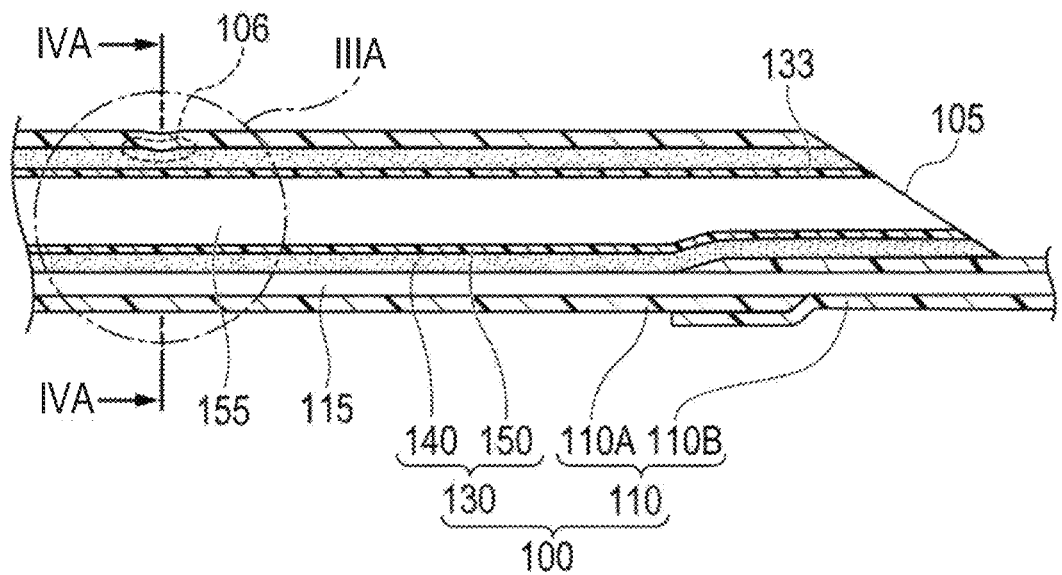
FIG. 2B is an enlarged sectional view of a portion surrounded by a broken line portion IIB in FIG. 1.

As illustrated in FIGS. 2A and 2B, the shaft 100 has an outer tube shaft 110 including a lumen (inflation lumen) 115, and an inner tube shaft 130 including a guide wire lumen 155 which is located in the lumen 115 of the outer tube shaft 110 and into which the guide wire 200 is inserted.

As illustrated in FIGS. 1 and 2B, the shaft 100 has a proximal opening portion (proximal opening portion of the inner tube shaft 130) 105 which communicates with the guide wire lumen 155 of the inner tube shaft 130. The proximal opening portion 105 is formed in the vicinity of a proximal portion 133 (proximal portion of a first layer 140 and a second layer 150 of the inner tube shaft 130) of the inner tube shaft 130.

As illustrated in FIG. 2B, the outer tube shaft 110 has a distal side shaft 110A and a proximal side shaft 110B connected to the proximal side of the distal side shaft 110A.

In accordance with an exemplary embodiment, the distal side shaft 110A and the proximal side shaft 110B are integrally connected (fusion-bonded) to the inner tube shaft 130 in the vicinity of the proximal opening portion 105 of the shaft 100.

A lumen (not illustrated) of the distal side shaft 110A and a lumen (not illustrated) of the proximal side shaft 110B has the lumen (inflation lumen) 115 which communicates with an inflatable space 167 of the balloon 160 in a state where the distal side shaft 110A and the proximal side shaft 110B are connected to each other.

As illustrated in FIG. 2A, the inner tube shaft 130 has a distal member 180 located on the distal side. The distal member 180 has a lumen 181 into which the guide wire 200 can be inserted.

The inner tube shaft 130 has the distal member 180 on the distal side. In this manner, the biological organ can be prevented from being damaged when a distal end of the balloon catheter 10 comes into contact with the biological lumen (such as an intravascular wall). For example, the distal member 180 can be formed of a flexible resin material. However, a material of the distal member 180 is not particularly limited as long as the distal member 180 can be fixed to the inner tube shaft 130.

As illustrated in FIG. 2A, the guide wire lumen 155 communicates with the lumen 181 of the distal member 180 on the distal side of the inner tube shaft 130. In addition, as illustrated in FIG. 2B, the guide wire lumen 155 communicates with the proximal opening portion 105 on the proximal side of the inner tube shaft 130. The guide wire lumen 155 is formed on an inner surface side of the second layer 150 of the inner tube shaft 130 (to be described later).

As illustrated in FIG. 2A, the balloon 160 has a distal portion 161 fixed to a distal portion 131 of the inner tube shaft 130, a proximal portion 163 fixed to a distal portion 111 of the outer tube shaft 110, and an intermediate portion 166 which forms a largest outer diameter portion formed between the distal portion 161 and the proximal portion 163 of the balloon 160. In addition, the balloon 160 has a distal side tapered portion 164 formed between the distal portion 161 and the intermediate portion 166, and a proximal side tapered portion 165 formed between the proximal portion 163 and the intermediate portion 166.

The balloon 160 forms the inflatable space 167 which communicates with the lumen 115 between the balloon 160 and an outer peripheral surface of the shaft 100. In accordance with an exemplary embodiment, the balloon 160 can be inflated in a radial direction intersecting the axial direction, if (i.e., when) a fluid flows into the inflatable space 167.

As illustrated in FIG. 2A, the inner tube shaft 130 can have a contrast marker 170 which indicates a substantially center position in the axial direction of the intermediate portion 166 of the balloon 160. For example, the contrast marker 170 can be formed of metal such as platinum, gold, silver, iridium, titanium, and tungsten, or an alloy of platinum, gold, silver, iridium, titanium, and tungsten. The contrast marker 170 may be located at a position indicating a boundary portion between the distal side tapered portion 164 and the intermediate portion 166 in the inner tube shaft 130, and a position indicating a boundary portion between the proximal side tapered portion 165 and the intermediate portion 166 in the inner tube shaft 130.

As illustrated in FIG. 1, for example, the hub 190 has a port 191 which can be connected in a liquid-tight and airtight manner to a supply device (not illustrated) such as an indeflator for supplying a fluid (for example, a contrast agent or a saline solution). For example, the port 191 of the hub 190 can be configured to include a known luer taper configured so that a tube is connectable to the port 191 of the hub 190 and separable from the port 191 of the hub 190.

Next, the outer tube shaft 110 and the inner tube shaft 130 will be described in detail.

As illustrated in FIGS. 2A and 2B, in accordance with an exemplary embodiment, the inner tube shaft 130 includes a first layer 140 and a second layer 150. As shown in FIGS. 2A and 2B, the second layer 150 is located on the inner surface side of the first layer 140. Specifically, the inner tube shaft 130 has the first layer 140 and the second layer 150 located on the inner surface side of the first layer 140 and existing coaxially with the first layer 140.

The coaxial described above means that the respective layers 140 and 150 are arranged so that an axis passing through the distal side of the first layer 140 and an axis passing through the distal side of the second layer 150 extend substantially parallel to each other. The term does not mean only a state where the axes of the respective layers 140 and 150 strictly overlap each other.

In accordance with an exemplary embodiment, the material of first layer 140 of the inner tube shaft 130 is a material having an optical absorption property (i.e., light absorption property) greater than (i.e., higher than) the outer tube shaft 110 and the second layer 150 of the inner tube shaft 130. In addition, the material of the second layer 150 of the inner tube shaft 130 is a material having a melting point greater than (i.e., higher than) that of the first layer 140 of the inner tube shaft 130. A specific example of a configuration material of the outer tube shaft 110 and a configuration material of the inner tube shaft 130 will be described later.

Figure 3:
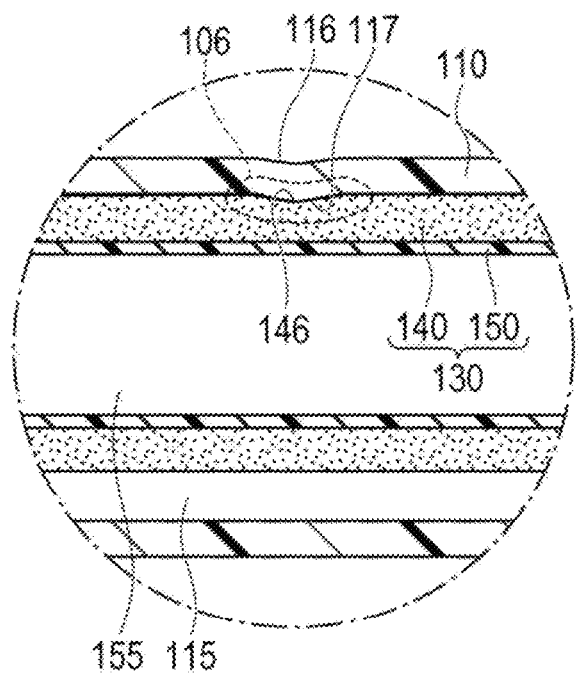
FIG. 3 is an enlarged view illustrating a portion surrounded by a broken line portion IIIA in FIG. 2B.
Figure 4:
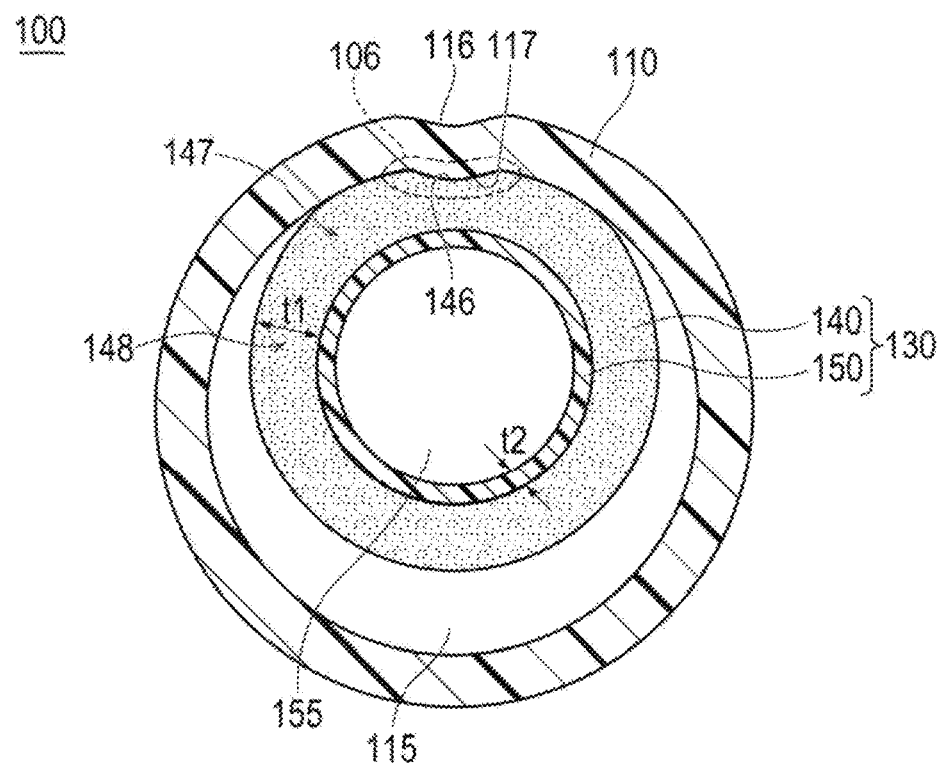
FIG. 4 is a sectional view taken along an arrow line IVA-IVA illustrated in FIG. 2B

As illustrated in FIGS. 2B, 3, and 4, in accordance with an exemplary embodiment, while the outer tube shaft 110 is recessed toward the inner tube shaft 130 side (axial center side of the shaft 100), the outer tube shaft 110 can be fusion-bonded to the first layer 140 of the inner tube shaft 130. FIG. 3 is an enlarged view of a portion surrounded by a broken line portion 3A in FIG. 2B, and FIG. 4 is a sectional view (sectional view perpendicular to the axial direction of the inner tube shaft 130) along an arrow line IVA-IVA illustrated in FIG. 2B.

As illustrated in FIGS. 3 and 4, the shaft 100 has a fusion-bonded portion 106 in a portion of the outer tube shaft 110 fusion-bonded to the first layer 140 of the inner tube shaft 130 in a state where the outer tube shaft 110 is recessed toward the inner tube shaft 130 side.

For example, the fusion-bonded portion 106 can be located (i.e., separated) to the proximal side of the shaft 100, for example, between 5 mm to 220 mm in the axial direction from the proximal portion 163 of the balloon 160.

In accordance with an exemplary embodiment, an axial position or an axial length (i.e., range or distance from the proximal portion 163 of the balloon 160) for forming the fusion-bonded portion 106, and the number of the fusion-bonded portions 106 formed in one shaft 100 are not particularly limited as long as the lumen 115 of the outer tube shaft 110 is not closed by the fusion-bonded portion 106.

As illustrated in FIG. 4, in accordance with an exemplary embodiment, the thickness of the first layer 140 of the inner tube shaft 130 increases toward the fusion-bonded portion 106, in a cross section perpendicular to the axial direction of the inner tube shaft 130.

When the fusion-bonded portion 106 is formed by fusion-bonding the outer tube shaft 110 and the inner tube shaft 130 to each other, the first layer 140 of the inner tube shaft 130 is fusion-bonded to the outer tube shaft 110 in a state of partially coming into contact with the outer tube shaft 110. After fusion-bonded, the first layer 140 of the inner tube shaft 130 has a concave portion 146, a thickness increasing portion 147, and a thickness maintaining portion 148.

In accordance with an exemplary embodiment, the concave portion 146 is formed in the fusion-bonded portion 106 and a peripheral portion of the fusion-bonded portion 106. The concave portion 146 can be formed as follows. In a state where the first layer 140 is in contact with (is pressed against) the outer tube shaft 110, heat is applied to the first layer 140. In this manner, a resin of (i.e., configuring) the first layer 140 flows into a periphery of the first layer 140 from a contact location 106a (refer to FIG. 6) between the first layer 140 and the outer tube shaft 110. Therefore, the concave portion 146 forms a thinnest portion in the first layer 140 after the fusion-bonded portion 106 is formed.

In accordance with an exemplary embodiment, the thickness increasing portion 147 of the first layer 140 can include a resin of (i.e., configuring) the first layer 140 which flows into a side in the circumferential direction of the first layer 140 as the concave portion 146 is formed. That is, the thickness increasing portion 147 of the first layer 140 is formed as follows. The resin of the portion having the concave portion 146 of the first layer 140 flows into the thickness increasing portion 147 of the first layer 140 so as to increase an original thickness (thickness indicated by t1 in the drawing) of the first layer 140. Therefore, the thickness of the thickness increasing portion 147 gradually increases as the thickness increasing portion 147 is closer to the fusion-bonded portion 106 of the first layer 140 along the circumferential direction of the first layer 140.

In accordance with an exemplary embodiment, a thickness maintaining portion 148 of the first layer 140 is formed in a portion which is hardly (i.e., not to a significant degree) affected by the heat applied to the first layer 140 of the inner tube shaft 130 when the fusion-bonded portion 106 is formed. That is, the thickness maintaining portion 148 is formed in a direction away from the fusion-bonded portion 106 from the thickness increasing portion 147 in the circumferential direction of the first layer 140.

As illustrated in FIG. 3, the outer tube shaft 110 has a concave portion 116 and a convex portion 117.

In accordance with an exemplary embodiment, the concave portion 116 of the outer tube shaft 110 is formed so that the outer surface of the outer tube shaft 110 is recessed toward the inner tube shaft 130 side. The convex portion 117 of the outer tube shaft 110 is formed so that the inner surface of the outer tube shaft 110 protrudes to the inner tube shaft 130 side. The concave portion 116 and the convex portion 117 of the outer tube shaft 110 are formed by applying the heat to the outer tube shaft 110 and the inner tube shaft 130 in a state where the outer tube shaft 110 and the inner tube shaft 130 are brought into contact with each other when the fusion-bonded portion 106 is formed.

As illustrated in FIG. 4, the first layer 140 of the inner tube shaft 130 forms an outermost layer of the inner tube shaft 130. Therefore, the first layer 140 of the inner tube shaft 130 is interposed between the inner surface of the outer tube shaft 110 and the outer surface of the second layer 150 of the inner tube shaft 130.

As illustrated in FIG. 4, in accordance with an exemplary embodiment, the second layer 150 of the inner tube shaft 130 is thinner than the first layer 140 of the inner tube shaft 130, in a cross section perpendicular to the axial direction of the inner tube shaft 130.

The thin inner tube shaft 130 described above means that the thickness of the second layer 150 before the fusion-bonded portion 106 is formed is less than (i.e., thinner than) the thickness of the first layer 140 before the fusion-bonded portion 106 is formed. The thickness of the first layer 140 before the fusion-bonded portion 106 is formed is substantially the same as the thickness of the thickness maintaining portion 148.

The thickness (thickness of the thickness maintaining portion 148) t1 of the first layer 140 of the inner tube shaft 130 can be 0.01 mm to 0.1 mm, for example. A thickness t2 of the second layer 150 of the inner tube shaft 130 can be 0.005 mm to 0.01 mm, for example.

In accordance with an exemplary embodiment, the second layer 150 of the inner tube shaft 130 can contribute to a decrease in sliding resistance of the guide wire 200 inserted into the guide wire lumen 155. Therefore, even if the thickness t2 of the second layer 150 is formed to be relatively thin, there is no disadvantage in performance of the balloon catheter 10.

Next, a configuration material of the balloon catheter 10 will be described.

For example, the balloon 160 can be formed of polyamide resin, polyamide elastomer resin, or a blend of polyamide resin and polyamide elastomer resin, in addition to thermoplastic elastomer such as vinyl chloride, polyurethane elastomer, polystyrene elastomer, styrene-ethylene-butylene-styrene copolymer (SEBS), and styrene-ethylene-propylene-styrene copolymer (SEPS), thermoplastic resins such as PET, thermosetting resins such as rubber and silicone elastomer. In addition, the balloon 160 may be a multilayer balloon having two or more layers. In accordance with an exemplary embodiment, it can be preferable that the balloon 160 is formed of the polyamide resin, polyamide elastomer resin, or a blend of polyamide resin and polyamide elastomer resin. In this case, in the balloon 160, the outer tube shaft 110 can be formed of polyamide resin and the first layer 140 of the inner tube shaft 130 can be formed of a polyamide layer, a fixing force (fusion-bonding force) between the outer tube shaft 110 and the inner tube shaft 130 can be relatively strengthened.

In accordance with an exemplary embodiment, for example, the distal member 180 of the inner tube shaft 130 can be formed of polyolefin (for example, polyethylene, polypropylene, polybutene, ethylene-propylene copolymer, ethylene-vinyl acetate copolymer, ionomer, or a mixture of the above-described two or more materials), polymeric materials such as polyvinyl chloride, polyamide, polyamide elastomer, polyurethane, polyurethane elastomer, polyimide, fluorocarbon resin, or a mixture polyolefin and polymeric materials, and alternatively, a multilayer tube having the above-described two or more polymeric materials. In accordance with an exemplary embodiment, it can be preferable that the distal member 180 of the inner tube shaft 130 is formed of a material softer than the materials forming the first layer 140 and the second layer 150 of the inner tube shaft 130.

For example, the outer tube shaft 110 can be formed of a material containing a polyamide resin (polyamide-based resin). In accordance with an exemplary embodiment, the polyamide resin is not particularly limited as long as the polyamide resin has an acid amide bond (—CO—NH—) in the main chain. In accordance with an exemplary embodiment, the polyamide resin can be manufactured through polymerization (homopolymerization) of lactam or amino acid having a ring structure, or through condensation polymerization of dicarboxylic acid and diamine under the presence of a suitable catalyst.

In accordance with an exemplary embodiment, monomers that can be polymerized alone include ε-caprolactam, undecane lactam, lauryllactam, aminocaproic acid, 7-aminoheptanoic acid, 11-aminoundecanoic acid, 12-aminododecanoic acid, 9-aminononanoic acid, and piperidone.

In addition, dicarboxylic acid in a case of condensation polymerization of dicarboxylic acid and diamine can include adipic acid, sebacic acid, dodecanedicarboxylic acid, glutaric acid, terephthalic acid, 2-methylterephthalic acid, isophthalic acid, and naphthalenedicarboxylic acid. Diamine can include tetramethylenediamine, hexamethylenediamine, nonamethylenediamine, decamethylenediamine, undecamethylenediamine, dodecamethylenediamine, paraphenylenediamine, and metaphenylenediamine.

In accordance with an exemplary embodiment, a polyamide elastomer resin may be used as the polyamide resin. For example, the polyamide elastomer resin can include a block copolymer of polyamide (hard segment) and polyether (soft segment). More specifically, for example, the polyamide elastomer resin can include a block copolymer of nylon 11 and polytetramethylene glycol or a block copolymer of nylon 12 and polytetramethylene glycol.

As to the polyamide resin, in accordance with an exemplary embodiment, it can be preferable to use a polyamide resin having no segment other than polyamide. For example, nylon 4, 6, 7, 8, 11, 12, 6.6, 6.9, 6.10, 6.11, 6.12, 6T, 6/6.6, 6/12, 6/6T, and 6T/61 can be used. Among the above-described materials, nylon 11 and nylon 12 (polyamide 12), for example, are more preferably used as the polyamide resin.

In accordance with an exemplary embodiment, an end of the polyamide resin may be sealed with a carboxyl group or an amino group. The above-described polyamide resin can be used alone, or can be used in combination of two or more types.

For example, commercially available products that may be used as the polyamide resin, include Daiamid® series (L1640, L1840, L1940, L1940W, L2140, L2140W, and L2121) and Vestamid® series (hitherto, Daicel-Evonik Ltd.), Pebax® series (Arkema K.K.), Amilan® series (Toray Industries, Inc.), Leona® series (Asahi Kasei Corporation Ltd.), UBEnylon® series (Ube Industries, Ltd.), Reny® series (Mitsubishi Engineering-Plastics Corporation), Zytel® series (DuPont Corporation), Grilamid® and Grilflex® (hitherto, EMS-CHEMIE (Japan) Ltd.), and Rilsamid® (Arkema K.K.). In addition, the commercially available polyamide-based resin described above may be used alone, or a blend of two or more polyamide-based resins may be used.

In accordance with an exemplary embodiment, the weight-average molecular weight of the polyamide-based resin is preferably 10,000 to 500,000, and more preferably 15,000 to 300,000. As the "weight-average molecular weight" of the polyamide-based resin, the present disclosure adopts a value measured by gel permeation chromatography (GPC).

In accordance with an exemplary embodiment, the material of the outer tube shaft 110 is not particularly limited as long as the optical absorption property of the outer tube shaft 110 is lower than the optical absorption property of the first layer 140 of the inner tube shaft 130. For example, the outer tube shaft 110 can be formed to be transparent (including colored transparency). When the outer tube shaft 110 and the first layer 140 of the inner tube shaft 130 are fusion-bonded to each other, it is preferable that the outer tube shaft 110 is formed of a transparent (particularly, colorless and transparent) resin so that heat generating light can be efficiently applied to the first layer 140 of the inner tube shaft 130 after passing through the outer tube shaft 110.

For example, the first layer 140 of the inner tube shaft 130 can be formed of a polyamide layer containing a pigment. With regard to the polyamide resin which can be preferably used for the first layer 140 of the inner tube shaft 130 and a molecular weight of the polyamide resin of the first layer 140, those described as the material of the outer tube shaft 110 can be used for the first layer 140. From a viewpoint of fusion-bonding performance, in accordance with an exemplary embodiment, it can be preferable that the same polyamide-based resin is used for the outer tube shaft 110 and the first layer 140 of the inner tube shaft 130.

In accordance with an exemplary embodiment, the pigment contained in the first layer 140 of the inner tube shaft 130 can be obtained by adding various colors such as a black, red, green, blue, yellow, purple, or white color to the first layer 140. The color of the first layer 140 colored by the pigment is not particularly limited as long as the first layer 140 has an optical absorption property greater than the outer tube shaft 110 and the second layer 150. However, for example, in accordance with an exemplary embodiment, from a viewpoint of improving the optical absorption property, it is preferable to use the black color.

Examples of the pigment contained in the first layer 140 of the inner tube shaft 130 may include inorganic pigments such as carbon black, titanium oxide, barium sulfate, iron oxide (black iron oxide, yellow iron oxide, and red iron oxide), chromium oxide, ultramarine blue (ultramarine blue and ultramarine violet color), nickel titanium yellow, Prussian blue, Milori blue, cobalt blue, Viridian, and molybdenum red. Examples of the pigment contained in the first layer 140 of the inner tube shaft 130 may also include organic pigments such as quinacridone (for example, quinaclide red), perylene (for example, perylene red), anthraquinone (for example, anthraquinone yellow), azo (for example, condensed azo yellow organic pigment), and phthalocyanine pigment (for example, halogenated phthalocyanine such as copper phthalocyanine and high chloride copper phthalocyanine). The above pigments can be used alone, or can be used in combination of two or more types.

In addition, the pigment may be contained in the first layer 140 of the inner tube shaft 130 in a form of a colorant containing a predetermined dispersant for dispersing the pigment into the resin.

For example, the second layer 150 of the inner tube shaft 130 can be formed of a fluorine resin such as PTEF, ETFE, and PFA. The second layer 150 of the inner tube shaft 130 may employ a fluorine resin alone, or may employ a combination of two or more fluorine resins. In addition, in a case where the first layer 140 of the inner tube shaft 130 is formed of the polyamide-based resin, the second layer 150 of the inner tube shaft 130 may be formed of an adhesive fluorine resin (a resin having low friction coefficient characteristics, which are inherent in fluorocarbon resin, and having an improved affinity for the polyamide resin, which can be created by introducing functional groups into fluorocarbon resin). For example, the adhesive fluorine resin can be a homopolymer or copolymer having a tetrafluoroethylene unit, and can include the resin having functional groups such as a carbonate group, a carboxylic acid halide group, a hydroxyl group, a carboxyl group, and an epoxy group at a terminal or a side chain. For example, the commercially available product can include Neoflon EFEP (Daikin Industries, Ltd.), Neoflon CPT (Daikin Industries, Ltd.), and LM-ETFE AH2000 (Asahi Glass Co., Ltd.). In a case where the first layer 140 of the inner tube shaft 130 is formed of a polyamide-based resin, the second layer 150 of the inner tube shaft 130 may include (i.e., employ) the adhesive fluorine resin alone, or may employ a combination of two or more adhesive fluorine resins.

In accordance with an exemplary embodiment, the second layer 150 (resin as a main raw material for forming the second layer 150) of the inner tube shaft 130 is preferably formed of a material whose melting point is at least 10° C. (degrees Celsius) greater than (i.e. higher than) the melting point of the first layer 140 (resin as a main raw material for forming the first layer 140) of the inner tube shaft 130, and is more preferably formed of a material whose melting point is at least 12° C. greater than (i.e., higher than) the melting point of the first layer 140 of the inner tube shaft 130. As will be described later in examples, if a difference between the melting points is at least 10° C., the second layer 150 can be preferably prevented from being melted when the fusion-bonded portion 106 is formed. In accordance with an exemplary embodiment, the difference between the melting point of the second layer 150 of the inner tube shaft 130 and the melting point of the first layer 140 of the inner tube shaft 130 is preferably 80° C. or lower. In a case where the inner tube shaft 130 having the first layer 140 and the second layer 150 is molded by means of co-extrusion molding, if the difference between the melting point of the second layer 150 of the inner tube shaft 130 and the melting point of the first layer 140 of the inner tube shaft 130 is 80° C. or lower, the inner tube shaft 130 can be rather easily formed.

In accordance with an exemplary embodiment, the material of the second layer 150 of the inner tube shaft 130 is not particularly limited as long as the optical absorption property of the second layer 150 of the inner tube shaft 130 is lower than the optical absorption property of the first layer 140 of the inner tube shaft 130. However, for example, the second layer 150 of the inner tube shaft 130 can be formed to be colorless and transparent.

In accordance with an exemplary embodiment, the inner tube shaft 130 including the first layer 140 and the second layer 150, for example, can be formed using a core bar covered by a resin material, which forms the second layer 150 of the inner tube shaft 130. Thereafter, the core bar covered by the resin material for forming the second layer 150 is covered by the resin material for forming the first layer 140 of the inner tube shaft 130. Thereafter, the molding can be performed by removing the core bar from the inner tube shaft 130, which includes the first layer 140 and the second layer 150. Similarly, the inner tube shaft 130 including the first layer 140 and the second layer 150 can be formed as follows by means of the co-extrusion molding. For example, the resin material of (i.e., configuring) the first layer 140 of the inner tube shaft 130 and fine powder or coating dispersion (further containing the pigment for the first layer 140) of the resin material of (i.e., configuring the second layer 150 of the inner tube shaft 130 are prepared. A third layer 450 to be described later in a modification example can also be formed as follows. The core bar is covered by the resin material for forming the second layer 150. Thereafter, before the core bar is covered by the resin material for forming the first layer 140, the core bar covered by the resin material for forming the second layer 150 is covered by the resin material for forming the third layer 450. Similarly, the third layer 450 to be described later in the modification example can also be formed together with the first layer 140 and the second layer 150 by means of the co-extrusion molding.

Next, a method of manufacturing the balloon catheter 10 according to the present embodiment will be described.

First, a worker who manufactures the balloon catheter 10 supplies (prepares) the outer tube shaft 110, the inner tube shaft 130, and the balloon 160.

Figure 5:
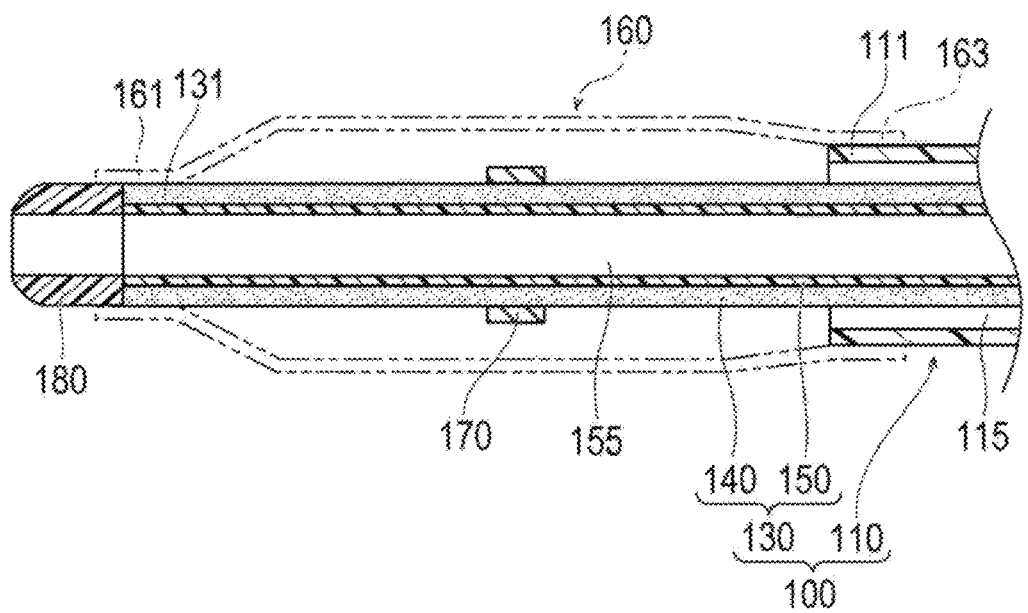
FIG. 5 is a sectional view for illustrating a method of manufacturing the balloon catheter according to the embodiment.

As illustrated in FIG. 5, the worker locates the inner tube shaft 130 so that the distal portion 131 of the inner tube shaft 130 protrudes from the distal end (distal opening portion) of the outer tube shaft 110. The worker fixes (for example, fusion-bonds) the balloon 160 to the distal side of the inner tube shaft 130 and the distal side of the outer tube shaft 110.

The outer tube shaft 110 (distal side shaft 110A and proximal side shaft 110B) and the inner tube shaft 130 may be prepared in a state where both the shafts 110 and 130 are fixed (for example, fusion-bonded) to each other in the vicinity of the proximal opening portion 105 of the shaft 100 while the inner tube shaft 130 protrudes from the distal end of the outer tube shaft 110. Alternatively, in a state where both the shafts 110 and 130 are not fixed to each other, both the shafts 110 and 130 may be prepared. Thereafter, both the shafts 110 and 130 are fixed to each other, and the worker may proceed to fixing work of the balloon 160. In addition, it is preferable to fix the distal member 180 to the distal end of the inner tube shaft 130 as illustrated in FIG. 5 before the fixing work of the balloon 160 is carried out.

Figure 6:
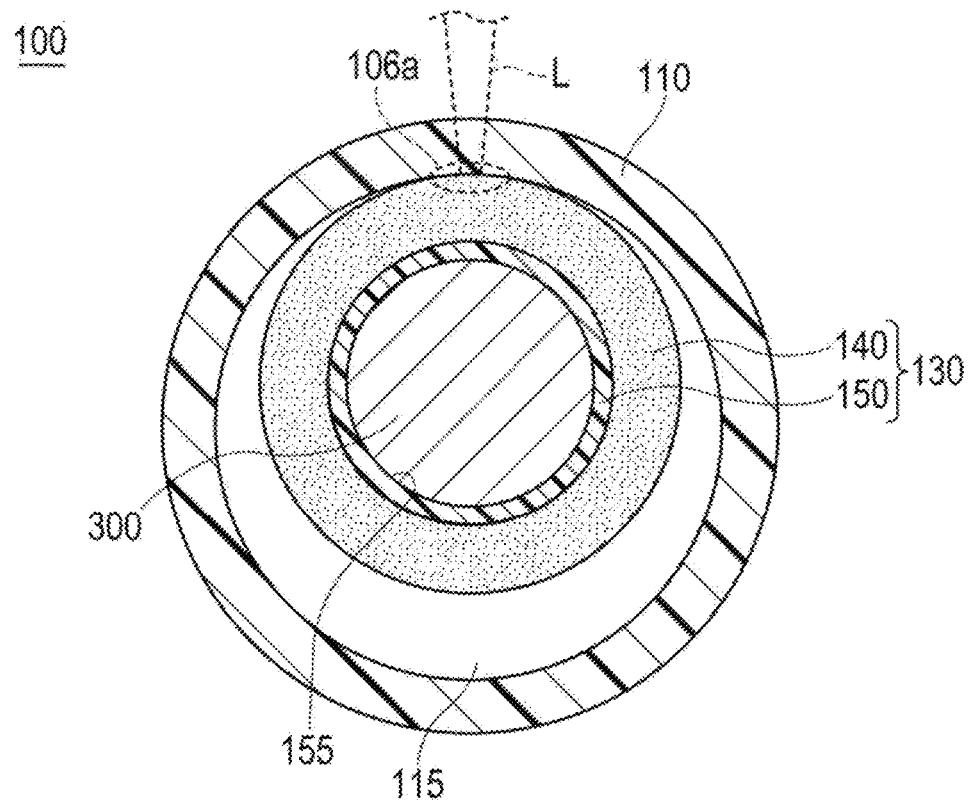
FIG. 6 is a sectional view for illustrating a method of manufacturing the balloon catheter according to the embodiment.

Next, as illustrated in FIG. 6, in a state where a portion of the outer surface of the inner tube shaft 130 is brought into contact with the inner surface of the outer tube shaft 110, the worker applies heat generating light L from the outer surface side of the outer tube shaft 110 to the contact location 106a (location including a boundary surface on which the outer surface of the inner tube shaft 130 comes into contact with the inner surface of the outer tube shaft 110) between the inner tube shaft 130 and the outer tube shaft 110. The outer surface of the inner tube shaft 130 and the inner surface of the outer tube shaft 110 can be brought into contact with each other as follows. For example, a predetermined jig (for example, the core bar 300 illustrated in FIG. 6) located on the inner surface side of the inner tube shaft 130 can be used. While the inner tube shaft 130 is pressed against the outer tube shaft 110 side, the outer tube shaft 110 is pressed against the inner tube shaft 130 side by using a predetermined jig located on the outer surface side of the outer tube shaft 110.

In accordance with an exemplary embodiment, the heat generating light L is not particularly limited as long as the first layer 140 of the inner tube shaft 130 can be melted. For example, a fiber laser (wavelength 1,070 nm), a YAG laser (wavelength 1,064 nm), or a laser diode (808 nm, 840 nm, and 940 nm) can be used to generate the heat generating light L.

In accordance with an exemplary embodiment, the heat generating light L applied from the outer surface side of the outer tube shaft 110 can be transmitted through the outer tube shaft 110, and is applied to the contact location 106a. The above-described transmission does not mean that the heat generating light L is not completely absorbed by the outer tube shaft 110. For example, the heat generating light may be partially absorbed by the outer tube shaft 110 to such an extent that the outer tube shaft 110 is not excessively melted.

In accordance with an exemplary embodiment, a portion of the first layer 140 (contact location 106a and the peripheral portion) of the inner tube shaft 130 absorbs the heat generating light L. Heat is generated so that the portion is melted. The melted portion of the first layer 140 forms the fusion-bonded portion 106 for fusion-bonding the inner tube shaft 130 and the outer tube shaft 110 to each other (refer to FIG. 4).

As described above, the material of the outer tube shaft 110 has a lower optical absorption property than the material of the first layer 140 of the inner tube shaft 130. Therefore, the outer tube shaft 110 has relatively low ability to absorb the heat generating light L applied from the outer surface side of the outer tube shaft 110, and the outer tube shaft 110 is less likely to be melted by the heat generating light L. Similarly to the outer tube shaft 110, the material of the second layer 150 of the inner tube shaft 130 has a lower optical absorption property than the material of the first layer 140 of the inner tube shaft 130. Therefore, the second layer 150 of the inner tube shaft 130 has relatively low ability to absorb the heat generating light L, and the second layer 150 is less likely to be melted by the heat generating light L. Furthermore, the material of the second layer 150 of the inner tube shaft 130 can be a material having a melting point greater than (i.e. higher than) the melting point of the material of the first layer 140. Accordingly, the second layer 150 can be preferably prevented from being melted by the heat generating light L or due to the influence of the heat generated in the first layer 140.

As illustrated in FIG. 4, if the fusion-bonded portion 106 is formed in the shaft 100, the concave portion 146 is formed in the vicinity of the fusion-bonded portion 106 in the first layer 140 of the inner tube shaft 130. The thickness increasing portion 147 whose thickness increases toward the concave portion 146 is formed within a prescribed certain range in the circumferential direction from the concave portion 146. In addition, the thickness maintaining portion 148 in which the thickness of the first layer 140 is maintained regardless of the presence or absence of the fusion-bonded portion 106 is formed at a position separated as much as a prescribed distance in the circumferential direction from the concave portion 146 and the thickness increasing portion 147.

After the fusion-bonded portion 106 is formed, the worker can manufacture the balloon catheter 10 by attaching the hub 190 or a strain relief portion, for example.

Next, an operation of the balloon catheter 10 and the method of manufacturing the balloon catheter 10 according to the present embodiment will be described.

The balloon catheter 10 according to the present embodiment includes the outer tube shaft 110 having the lumen 115, the inner tube shaft 130 located in the lumen 115 of the outer tube shaft 110, and the balloon 160 fixed to the distal side of the inner tube shaft 130 and the distal side of the outer tube shaft 110. In addition, the inner tube shaft 130 has the first layer 140 and the second layer 150 located on the inner surface side of the first layer 140. The outer tube shaft 110 is fusion-bonded to the first layer 140 and recessed toward the inner tube shaft 130 side. The first layer 140 is formed of a material having an optical absorption property greater than (i.e., higher than) the optical absorption property of the material of the outer tube shaft 110 and the second layer 150. Then, the second layer 150 is formed of a material having a melting point greater than (i.e. higher than) the melting point of the material of the first layer 140.

In manufacturing the balloon catheter 10 configured as described above, the heat generating light is applied from the outer surface side of the outer tube shaft 110. In this manner, the heat generating light is absorbed by the first layer 140 of the inner tube shaft 130 having the higher optical absorption property than the outer tube shaft 110 and the second layer 150 of the inner tube shaft 130. In this manner, the first layer 140 of the inner tube shaft 130 is melted, and the inner tube shaft 130 and the outer tube shaft 110 are fusion-bonded to each other. Then, when the inner tube shaft 130 and the outer tube shaft 110 are fusion-bonded to each other, the outer surface of the outer tube shaft 110 and the inner surface (inner surface of the second layer 150) of the inner tube shaft 130 are less likely to be thermally affected by heat generation of the first layer 140. Accordingly, sliding ability of the guide wire 200 passing through the guide wire lumen 155 of the inner tube shaft 130 can be prevented from being degraded, or a leakage can be prevented from occurring in the lumen 115 of the outer tube shaft 110.

In addition, the second layer 150 of the inner tube shaft 130 is thinner than the first layer 140 of the inner tube shaft 130, in a cross section perpendicular to the axial direction of the inner tube shaft 130. Therefore, the thickness of the second layer 150 of the inner tube shaft 130 can be prevented from increasing, and the diameter of the guide wire lumen 155 can be prevented from being narrowed.

In addition, the second layer 150 of the inner tube shaft 130 is formed of a material whose melting point is at least 10° C. greater than (i.e. higher than) the melting point of the material of the first layer 140. Therefore, the second layer 150 of the inner tube shaft 130 can help prevent the second layer 150 from being melted due to the heat generating light or due to the influence of the heat generated in the first layer 140.

In addition, the first layer 140 of the inner tube shaft 130 forms the outermost layer of the inner tube shaft 130. Therefore, the worker who manufactures the balloon catheter 10 can cause the heat generating light applied from the outer surface side of the outer tube shaft 110 to more reliably reach the first layer 140, and the first layer 140 of the inner tube shaft 130 can be rather easily melted.

In addition, the thickness of the first layer 140 of the inner tube shaft 130 increases toward the fusion-bonded portion 106 between the outer tube shaft 110 and the inner tube shaft 130, in the cross section perpendicular to the axial direction of the inner tube shaft 130. Therefore, when stress concentration occurs in the vicinity of the fusion-bonded portion 106, the balloon catheter 10 can help prevent the first layer 140 from starting to be broken in the vicinity of the fusion-bonded portion 106.

In accordance with an exemplary embodiment, the method of manufacturing the balloon catheter 10 according to the present embodiment supplies the outer tube shaft 110, the inner tube shaft 130, and the balloon 160 to be fixed to the distal side of the inner tube shaft 130 and the distal side of the outer tube shaft 110. In addition, the inner tube shaft 130 has the first layer 140 and the second layer 150 located on the inner surface side of the first layer 140. The first layer 140 is formed of the material having the high optical absorption property than optical absorption property of the material of the outer tube shaft 110 and the second layer 150. The second layer 150 is formed of the material having a melting point greater than (i.e. higher than) the melting point of the material of the first layer 140. In addition, the inner tube shaft 130 is located so that the distal portion 131 of the inner tube shaft 130 protrudes from the distal end of the outer tube shaft 110, and the balloon 160 is fixed to the distal side of the inner tube shaft 130 and the distal side of the outer tube shaft 110. In addition, in a state where a portion of the outer surface of the inner tube shaft 130 is brought into contact with the inner surface of the outer tube shaft 110, the heat generating light is applied from the outer surface side of the outer tube shaft 110 to the contact location 106a between the inner tube shaft 130 and the outer tube shaft 110. A portion of the first layer 140 absorbs the heat generating light, and the heat is generated. In this manner, the first layer 140 is melted, thereby fusion-bonding the outer tube shaft 110 and the inner tube shaft 130 to each other.

According to the method of manufacturing the balloon catheter 10, when the outer tube shaft 110 and the inner tube shaft 130 are fusion-bonded to each other, the heat generating light can be applied from the outer surface side of the outer tube shaft 110. In accordance with an exemplary embodiment, the heat generating light is absorbed by the contact location 106a between the inner surface of the outer tube shaft 110 and the outer surface of the inner tube shaft 130. If the first layer 140 of the inner tube shaft 130 absorbs the heat generating light, the inner tube shaft 130 and the outer tube shaft 110 are melted and fusion-bonded to each other. Therefore, the worker who manufactures the balloon catheter 10 carries out relatively simple work for applying the heat generating light toward the outer tube shaft 110 and the inner tube shaft 130. In this manner, while the outer surface of the outer tube shaft 110 and the inner surface of the inner tube shaft 130 can be prevented from being excessively affected by the heat generation, the inner tube shaft 130 and the outer tube shaft 110 can be fusion-bonded to each other.

Next, a modification example according to the above-described embodiment will be described. Elements the same as those according to the above-described embodiment are applicable to members or manufacturing processes which are not particularly described in the modification example, and thus, description of those elements will be omitted.

Figure 7:
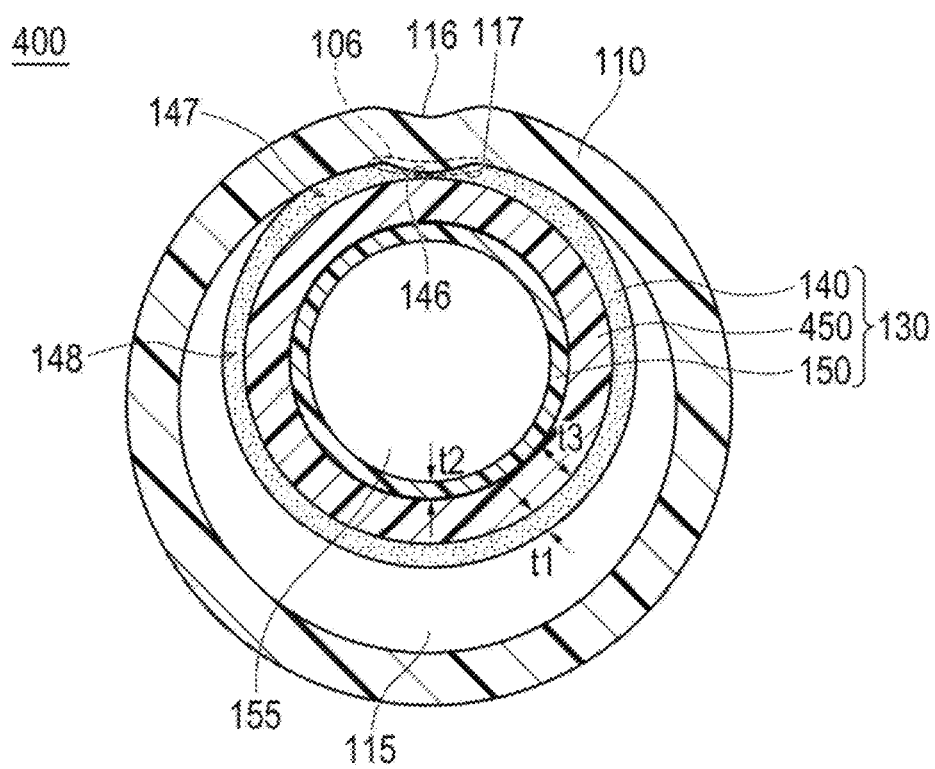
FIG. 7 is a sectional view illustrating a shaft of a balloon catheter according to a modification example.

FIG. 7 is a view illustrating a shaft 400 of the balloon catheter according to the modification example. FIG. 7 is an axially orthogonal sectional view (sectional view corresponding to FIG. 4) of the shaft 400.

The shaft 400 according to the modification example is different from the above-described embodiment in that the inner tube shaft 130 has a different configuration.

In accordance with an exemplary embodiment, the inner tube shaft 130 has a third layer 450 between the first layer 140 and the second layer 150. In addition, the third layer 450 is formed of a material having a greater affinity or higher affinity (i.e., chemical affinity or chemical attraction) for the second layer 150 than the first layer 140. The third layer 450 is preferably formed of a material having a greater affinity or higher affinity (i.e., chemical affinity) for the second layer 150 than the first layer 140 and having an affinity (i.e., chemical affinity) for the first layer 140 equal to or greater than that of the second layer 150.

For example, the first layer 140 and the second layer 150 can be formed of any of the materials as listed above in the embodiment.

For example, the third layer 450 can be formed of the polyamide resin listed as an example of the material of the first layer 140, other polyamide resins, or a polyamide elastomer resin (for example, Pebax which is the polyamide elastomer resin). In accordance with an exemplary embodiment, the material of the third layer 450 has a lower content of the pigment than content of the pigment of the first layer 140.

For example, the third layer 450 may be colored with a predetermined color pigment, similarly to the first layer 140. Alternatively, the third layer 450 may be transparent (including colored transparency or colorless transparency). However, it is preferable that the third layer 450 is formed of a material having the lower optical absorption property than the first layer 140. In a case where the third layer 450 is formed in this way, the third layer 450 can help prevent the heat from being transferred to the second layer 150, and can preferably help prevent the inner surface of the second layer 150 from being melted when the fusion-bonded portion 106 is formed.

For example, a thickness t3 of the third layer 450 can be thicker than the thickness t1 of the first layer 140 and the thickness t2 of the second layer 150. In a case where the third layer 450 is disposed between the first layer 140 and the second layer 150, for example, the thickness (thickness of the thickness maintaining portion 148) t1 of the first layer 140 of the inner tube shaft 130 can be formed to be 0.01 mm to 0.08 mm. For example, the thickness t2 of the second layer 150 of the inner tube shaft 130 can be formed to be 0.005 mm to 0.050 mm. For example, the thickness t3 of the third layer 450 can be formed to be thicker than the thickness t1 of the first layer 140 and the thickness t2 of the second layer 150.

As described above, the inner tube shaft 130 according to the modification example has the third layer 450 between the first layer 140 and the second layer 150. In addition, the third layer 450 has a greater affinity or higher affinity for the second layer 150 than the first layer 140. Therefore, it is possible to advantageously prevent separation (delamination) between the second layer 150 and the third layer 450.

Next, advantageous effects according to the present disclosure will be described with reference to the following examples and comparative examples. However, the technical scope of the present disclosure is not limited to the following examples. Unless otherwise specified, operations are performed at room temperature (for example, 25° C.).

Examples of First and Second Layers

In the examples, the outer tube shaft 110 and the inner tube shaft 130 having the first layer 140 and the second layer 150 were prepared. The heat generating light was applied so as to form the fusion-bonded portion described in the embodiment. As the heat generating light, a laser beam emitted by a YAG laser oscillator was used. After the fusion-bonded portion was formed, it was checked whether or not the second layer 150 had deformation (melting), which would cause leakage or a decrease in sliding ability of the guide wire 200.

The following outer tube shaft 110 and inner tube shaft 130 were prepared for examples and comparative examples.

Example 1

(1) The outer tube shaft 130 was formed by subjecting a polyamide resin (nylon 12 (Daiamid L1940W, Daicel-Evonik Ltd.)) to extrusion molding in which the resin was molded into a tubular shape having an inner diameter of 0.76 mm and a thickness of 0.06 mm. The molded outer tube shaft 110 was colorless and transparent.

(2) The inner tube shaft 130 was formed by coating a core bar having an outer diameter of 0.44 mm with a resin material for forming the second layer 150 (fluorine resin layer) and then subjecting the outer surface of the second layer 150 coating of the resin material to Tetra-Etch treatment. Thereafter, the Tetra-Etch-treated outer surface of the resin material of the second layer 150 was covered with a resin material for forming the first layer 140 (polyamide resin layer containing a pigment). Then, the core bar, which was covered with the resin materials forming the first layer 140 and the second layer 150, was removed from the first and second layers 140, 150, so that a two-layer tube having an inner diameter of 0.44 mm and a thickness of 0.07 mm was formed.

(3) The first layer 140 of the inner tube shaft 130 is a polyamide layer (nylon 12 (Daiamid L1940W, Daicel-Evonik Ltd.)) containing 0.25% by weight of carbon black (pigment) based on the total solid content of the polyamide resin layer and having a thickness of 0.06 mm. The first layer 140 of the inner tube shaft 130 was black. In addition, the melting point of the material of the first layer 140 is approximately 178° C.

(4) The second layer 150 of the inner tube shaft 130 is a fluorine resin layer (PTFE) with a thickness of 0.01 mm. The second layer 150 of the inner tube shaft 130 was colorless and transparent. In addition, the melting point of the second layer 150 is approximately 320° C. to 330° C. That is, the melting point of the second layer 150 is at least 10° C. greater than that of the first layer 140. The material of the second layer 150 contains no pigment.

Example 2

(1) The outer tube shaft 110 was formed by subjecting a polyamide resin (nylon 12 (Daiamid L1940W, Daicel-Evonik Ltd.)) to extrusion molding in which the resin was molded into a tubular shape having an inner diameter of 0.76 mm and a thickness of 0.06 mm. The molded outer tube shaft was colorless and transparent.

(2) The inner tube shaft 130 was formed by covering a core bar having an outer diameter of 0.44 mm with a resin material for forming the second layer 150 (fluorine resin layer) and then subjecting the outer surface of the second layer 150 coating of the resin material to Tetra-Etch treatment. Thereafter, the Tetra-Etch-treated outer surface of the resin material of the second layer 150 was covered with a resin material for forming the first layer 140 (polyamide resin layer containing a pigment). Then, the core bar, which was covered with the resin materials of the first and second layers 140, 150, was removed from the first and second layers 140, 150, so that a two-layer tube having an inner diameter of 0.44 mm and a thickness of 0.07 mm was formed.

(3) The first layer 140 of the inner tube shaft 130 is a polyamide layer (nylon 12 (Daiamid L1940W, Daicel-Evonik Ltd.)) containing 0.25% by weight of carbon black (pigment) based on the total solid content of the polyamide resin layer and having a thickness of 0.06 mm. The first layer 140 of the inner tube shaft 130 was black. In addition, the melting point of the material of the first layer 140 is approximately 178° C.

(4) The second layer 150 of the inner tube shaft 130 is a fluorine resin layer (ETFE) with a thickness of 0.01 mm. The second layer 150 of the inner tube shaft 130 was colorless and transparent. In addition, the melting point of the second layer 150 is approximately 260° C. to 270° C. That is, the melting point of the second layer 150 is at least 10° C. greater than that of the first layer 140. The material of the second layer 150 contains no pigment.

Example 3

(1) An outer tube shaft 110 was formed by subjecting a polyamide resin (nylon 12 (Daiamid L1940W, Daicel-Evonik Ltd.)) to extrusion molding in which the resin was molded into a tubular shape having an inner diameter of 0.76 mm and a thickness of 0.06 mm. The molded outer tube shaft 110 was colorless and transparent.

(2) The inner tube shaft 130 was formed by co-extrusion molding in which a two-layer tube having a first layer 140 (polyamide resin layer containing a pigment) and a second layer 150 (adhesive fluorine resin layer) was formed in a tubular shape having an inner diameter of 0.44 mm and a thickness of 0.07 mm.

(3) The first layer 140 of the inner tube shaft 130 is a polyamide layer (nylon 12 (Daiamid L1940W, Daicel-Evonik Ltd.)) containing 0.25% by weight of carbon black (pigment) based on the total solid content of the polyamide resin layer and having a thickness of 0.06 mm. The first layer 140 of the inner tube shaft 130 was black. In addition, the melting point of the material of the first layer 140 is approximately 178° C.

(4) The second layer 150 of the inner tube shaft 130 is an adhesive fluorine resin layer (Neoflon EFEP) with a thickness of 0.01 mm. The second layer 150 of the inner tube shaft 130 was colorless and transparent. In addition, the melting point of the second layer 150 is approximately 190° C. to 200° C. That is, the melting point of the second layer 150 is at least 10° C. greater than that of the first layer 140. The material of the second layer 150 contains no pigment.

Comparative Example 1

Shafts of Comparative Example 1 were prepared as in Example 1, except that the polyamide layer forming the first layer 140 of the inner tube shaft 130 contained no pigment. That is, in Comparative Example 1, no pigment is not contained in each of the first layer 140 and the second layer 150.

Comparative Example 2

Shafts of Comparative Example 2 were prepared as in Example 2, except that the polyamide layer forming the first layer 140 of the inner tube shaft 130 contained no pigment. That is, in Comparative Example 2, no pigment is contained in each of the first layer 140 and the second layer 150.

Comparative Example 3

Shafts of Comparative Example 3 were prepared as in Example 3, except that the polyamide layer forming the first layer 140 of the inner tube shaft 130 contained no pigment. That is, in Comparative Example 3, no pigment is contained in each of the first layer 140 and the second layer 150.

Comparative Example 4

(1) An outer tube shaft 110 was formed by subjecting a polyamide resin (nylon 12 (Daiamid L1940W, Daicel-Evonik Ltd.)) to extrusion molding in which the resin was molded into a tubular shape having an inner diameter of 0.76 mm and a thickness of 0.06 mm. The molded outer tube shaft 110 was colorless and transparent.

(2) An inner tube shaft 130 was formed by co-extrusion molding in which a two-layer tube having a first layer 140 (polyamide resin layer containing a pigment) and a second layer 150 (maleylation-modified polyolefin resin layer) was formed in a tubular shape having an inner diameter of 0.44 mm and a thickness of 0.07 mm.

(3) The first layer 140 of the inner tube shaft 130 is a polyamide layer (nylon 12 (Daiamid L1940W, Daicel-Evonik Ltd.)) containing 0.25% by weight of carbon black (pigment) based on the total solid content of the polyamide resin layer and having a thickness of 0.06 mm. The first layer 140 of the inner tube shaft 130 was black. In addition, the melting point of the material of the first layer 140 is approximately 178° C.

(4) The second layer 150 of the inner tube shaft 130 is a maleylation-modified polyolefin resin layer (MODIC H503 (Mitsubishi Chemical Holdings Group)) with a thickness of 0.01 mm. The second layer 150 of the inner tube shaft 130 was colorless and transparent. In addition, the melting point of the second layer 150 is approximately 100° C. to 130° C. That is, the material of the second layer 150 has a melting point lower than the melting point of the material of the first layer 140. The material of the second layer 150 contains no pigment.

Comparative Example 5

Shafts of Comparative Example 4 were prepared as in Example 4, except that the polyamide layer forming the first layer 140 of the inner tube shaft 130 contained no pigment. That is, in Comparative Example 5, no pigment is contained in each of the first layer 140 and the second layer 150.

Fusion-Bonding Result

As shown in Table 1, it was found that the first and second layers 140, 150 were satisfactorily fusion-bonded to each other in Examples 1, 2, and 3. It was also found that in Examples 1, 2, and 3, the second layer 150 did not undergo deformation (melting), which would cause leakage or a decrease in the sliding ability of the guide wire 200, because of the melting point of the second layer 150 was greater (at least 10° C.) than the melting point of the material of the first layer 140.

In Comparative Example 4, the second layer 150 underwent deformation (melting), which would cause leakage or a decrease in the sliding ability of the guide wire 200. This may be because the melting point of the second layer 150 is lower than the melting point of the material of the first layer 140.

The formation of a fusion-bonded portion was not observed in Comparative Examples 1, 2, 3, and 5. This may be because both the first and second layers 140, 150 containing no pigment allow part of the inner tube shaft 130 to absorb the laser beam so that no heat is generated in part of the inner tube shaft 130.

TABLE 1

|  | Fusion-bonding Result |
| --- | --- |
| Example 1 | Good |
| Example 2 | Good |
| Example 3 | Good |
| Comparative Example 1 | Poor |
| Comparative Example 2 | Poor |
| Comparative Example 3 | Poor |
| Comparative Example 4 | Poor |
| Comparative Example 5 | Poor |

The results indicate that when the first layer 140 of the inner tube shaft 130 is formed of a material having an optical absorption property greater than the optical absorption property of the outer tube shaft 110 and the second layer 150 of the inner tube shaft 130, and when the second layer 150 of the inner tube shaft 130 is formed of a material having a melting point greater than the melting point of the material of the first layer 140 of the inner tube shaft 130, the inner tube shaft 130 and the outer tube shaft 110 can be fusion-bonded to each other using a laser beam and the second layer 150 can be prevented from undergoing deformation (melting), which would cause leakage or a decrease in the sliding ability of the guide wire 200.

Examples of First, Second, and Third Layers

In the examples, an outer tube shaft 110 and an inner tube shaft 130 having three layers: first layer 140, second layer 150, and a third layer 450 were prepared, and heat generating light was applied so that a fusion-bonded portion was formed as described in the embodiment. Unless otherwise specified, the conditions are the same as those for the example of the inner tube shaft 130 having the two layers: the first and second layers.

Example 1

(1) An outer tube shaft 110 was formed by subjecting a polyamide resin (nylon 12 (Daiamid L1940W, Daicel-Evonik Ltd.)) to extrusion molding in which the resin was molded into a tubular shape having an inner diameter of 0.76 mm and a thickness of 0.06 mm. The molded outer tube shaft 110 was colorless and transparent.

(2) An inner tube shaft 130 was formed by coating a core bar having an outer diameter of 0.44 mm with a resin material for forming the second layer 150 (fluorine resin layer) and then subjecting the outer surface of the second layer 150 coating of the resin material to Tetra-Etch treatment. Thereafter, the Tetra-Etch-treated outer surface of the resin material of the second layer 150 was covered with a resin material for forming the third layer 450 (polyamide resin layer), and then the outer surface of the resin material of the third layer 450 was covered with a resin material for forming the first layer 140 (polyamide resin layer containing a pigment). Then, the core bar, which was covered with the resin materials forming the first, second, and third layers, 140, 150, 450 was removed from the layers, so that a three-layer tube having an inner diameter of 0.44 mm and a thickness of 0.07 mm was formed.

(3) The first layer 140 of the inner tube shaft 130 is a polyamide layer (nylon 12 (Daiamid L1940W, Daicel-Evonik Ltd.)) containing 0.25% by weight of carbon black (pigment) based on the total solid content of the polyamide resin layer and having a thickness of 0.015 mm. The first layer 140 of the inner tube shaft 130 was black. In addition, the melting point of the material of the first layer 140 is approximately 178° C.

(4) The second layer 150 of the inner tube shaft 130 is a fluorine resin layer (PTFE) with a thickness of 0.01 mm. The second layer 150 of the inner tube shaft 130 was colorless and transparent. In addition, the melting point of the second layer 150 is approximately 320° C. to 330° C. That is, the melting point of the second layer 150 is at least 10° C. greater than the melting point of the first layer 140. The material of the second layer 150 contains no pigment.

(5) The third layer 450 of the inner tube shaft 130 is a polyamide layer (nylon 12 (Daiamid L1940W, Daicel-Evonik Ltd.)) with a thickness of 0.045 mm. The third layer 450 of the inner tube shaft 130 was colorless and transparent. In addition, the melting point of the third layer 450 is approximately 178° C. In addition, the material of the third layer 450 contains no pigment.

Example 2

Shafts of Example 2 were prepared as in Example 1, except that the second layer 150 was made of a fluorine resin (ETFE). The melting point of the material of the second layer 150 is approximately 260° C. to 270° C.

Example 3

Shafts of Example 3 were prepared as in Example 1, except that the third layer 450 was made of Pebax 7033 (Arkema K.K.). The third layer 450 of the inner tube shaft 130 was colorless and transparent. In addition, the melting point of the material of the third layer 450 is approximately 170° C. to 178° C. In addition, the material of the third layer 450 contains no pigment.

Example 4

Shafts of Example 4 were prepared as in Example 1, except that carbon black (pigment) was contained in the third layer 450. That is, in Example 4, the pigment is contained in the first and third layers 140, 450.

Example 5

(1) An outer tube shaft 110 was formed by subjecting a polyamide resin (nylon 12 (Daiamid L1940W, Daicel-Evonik Ltd.)) to extrusion molding in which the resin was molded into a tubular shape having an inner diameter of 0.76 mm and a thickness of 0.06 mm. The molded outer tube shaft 110 was colorless and transparent.

(2) An inner tube shaft 130 was formed by co-extrusion molding in which a three-layer tube having a first layer 140 (polyamide resin layer containing a pigment), a second layer 150 (adhesive fluorine resin layer), and a third layer 450 (polyamide resin layer) was formed in a tubular shape with an inner diameter of 0.44 mm and a thickness of 0.07 mm.

(3) The first layer 140 of the inner tube shaft 130 is a polyamide layer (nylon 12 (Daiamid L1940W, Daicel-Evonik Ltd.)) containing 0.25% by weight of carbon black (pigment) based on the total solid content of the polyamide resin layer and having a thickness of 0.015 mm. The first layer 140 of the inner tube shaft 130 was black. In addition, the melting point of the material of the first layer 140 is approximately 178° C.

(4) The second layer 150 of the inner tube shaft 130 is an adhesive fluorine resin layer (Neoflon ETEP) with a thickness of 0.01 mm. The second layer 150 of the inner tube shaft 130 was colorless and transparent. In addition, the melting point of the second layer 150 is approximately 190° C. to 200° C. That is, the melting point of the second layer 150 is at least 10° C. greater than the melting point of the material of the first layer 140. The material of the second layer 150 contains no pigment.

(5) The third layer 450 of the inner tube shaft 130 is a polyamide layer (nylon 12 (Daiamid L1940W, Daicel-Evonik Ltd.)) with a thickness of 0.045 mm. The third layer 450 of the inner tube shaft 130 was colorless and transparent. In addition, the melting point of the third layer 450 is approximately 178° C. In addition, the material of the third layer 450 contains no pigment.

Example 6

Shafts of Example 6 were prepared as in Example 5, except that the third layer was made of Pebax 7033 (Arkema K.K.). The third layer 450 of the inner tube shaft 130 was colorless and transparent. In addition, the melting point of the material of the third layer 450 is approximately 170° C. to 178° C. In addition, the material of the third layer 450 contains no pigment.

Example 7

Shafts of Example 7 were prepared as in Example 5, except that carbon black (pigment) was contained in the third layer 450. That is, in Example 7, the pigment is contained in the first and third layers 140, 450.

Comparative Example 1

Shafts of Comparative Example 1 were prepared as in Example 1, except that the first layer 140 contained no pigment. That is, in Comparative Example 1, no pigment is contained in each of the first, second, and third layers 140, 150, 450.

Comparative Example 2

Shafts of Comparative Example 2 were prepared as in Example 5, except that no pigment was contained in the first layer 140. That is, in Comparative Example 2, no pigment is contained in each of the first, second, and third layers 140, 150, 450.

Comparative Example 3

(1) An outer tube shaft 110 was formed by subjecting a polyamide resin (nylon 12 (Daiamid L1940W, Daicel-Evonik Ltd.)) to extrusion molding in which the resin was molded into a tubular shape having an inner diameter of 0.76 mm and a thickness of 0.06 mm. The molded outer tube shaft was colorless and transparent.

(2) An inner tube shaft 130 was formed by co-extrusion molding in which a three-layer tube having a first layer 140 (polyamide resin layer containing the pigment), a second layer 140 (polyolefin resin layer), and a third layer 450 (maleylation-modified polyolefin resin layer) was formed in a tubular shape with an inner diameter of 0.44 mm and a thickness of 0.07 mm.

(3) The first layer 140 of the inner tube shaft 130 is a polyamide layer (nylon 12 (Daiamid L1940W, Daicel-Evonik Ltd.)) containing 0.25% by weight of carbon black (pigment) based on the total solid content of the polyamide resin layer and having a thickness of 0.045 mm. The first layer 140 of the inner tube shaft 130 was black. In addition, the melting point of the material of the first layer 140 is approximately 178° C.

(4) The second layer 150 of the inner tube shaft 130 is a polyolefin resin layer (high density polyethylene (HB530, Mitsubishi Chemical Holdings Group)) with a thickness of 0.01 mm. In addition, the melting point of the second layer 150 is approximately 90° C. to 140° C. That is, the second layer 150 has a melting point lower than the melting point of the first layer 140. The second layer 150 contained carbon black (pigment).

(5) The third layer 450 of the inner tube shaft 130 is a maleylation-modified polyolefin layer (MODIC H503 (Mitsubishi Chemical Holdings Group)) with a thickness of 0.015 mm. The third layer 450 of the inner tube shaft 130 was colorless and transparent. In addition, the melting point of the third layer 450 is approximately 100° C. to 130° C. That is, the third layer 450 has a melting point lower than that of the first layer 140. The third layer 450 contains no pigment.

Comparative Example 4

Shafts of Comparative Example 4 were prepared as in Comparative Example 3, except that no pigment was contained in the second layer 150. That is, in Comparative Example 4, the pigment is contained in the first layer 140, and no pigment is contained in the second and third layers 150, 450.

Comparative Example 5

Shafts of Comparative Example 5 were prepared as in Comparative Example 3, except that no pigment was contained in the first layer 140. That is, in Comparative Example 5, the pigment is contained in the third layer 450, and no pigment is contained in the first and second layers 140, 150.

Comparative Example 6

Shafts of Comparative Example 6 were prepared as in Comparative Example 3, except that no pigment was contained in the first and second layers 140, 150. That is, in Comparative Example 6, no pigment was contained in each of the first, second, and third layers 140, 150, 450.

Comparative Example 7

(1) An outer tube shaft 110 was formed by subjecting a polyamide resin (nylon 12 (Daiamid L1940W, Daicel-Evonik Ltd.)) to extrusion molding in which the resin was molded into a tubular shape having an inner diameter of 0.76 mm and a thickness of 0.06 mm. The molded outer tube shaft was colorless and transparent.

(2) An inner tube shaft 130 was formed by co-extrusion molding in which a three-layer tube having a first layer 140 (polyamide resin layer containing a pigment), a second layer 150 (maleylation-modified polyolefin resin layer), and a third layer 450 (polyamide resin layer) was formed in a tubular shape with an inner diameter of 0.44 mm and a thickness of 0.07 mm.

(3) The first layer 140 of the inner tube shaft 130 is a polyamide layer (nylon 12 (Daiamid L1940W, Daicel-Evonik Ltd.)) containing 0.25% by weight of carbon black (pigment) based on the total solid content of the polyamide resin layer and having a thickness of 0.045 mm. The first layer 140 of the inner tube shaft 130 was black. In addition, the melting point of the material of the first layer 140 is approximately 178° C.

(4) The second layer of the inner tube shaft 130 is a maleylation-modified polyolefin layer (MODIC H503 (Mitsubishi Chemical Holdings Group)) with a thickness of 0.01 mm. The second layer 150 of the inner tube shaft 130 was colorless and transparent. In addition, the melting point of the second layer 150 is approximately 100° C. to 130° C. That is, the second layer 150 has a melting point lower than the melting point of the first layer 140. The third layer 450 contains no pigment.

(5) The third layer 450 of the inner tube shaft 130 is a polyamide layer (nylon 12 (Daiamid L1940W, Daicel-Evonik Ltd.)) with a thickness of 0.015 mm. The third layer 450 of the inner tube shaft 130 was colorless and transparent. In addition, the melting point of the third layer 450 is approximately 178° C. In addition, the material of the third layer 450 contains no pigment.

Comparative Example 8

Shafts of Comparative Example 8 were prepared as in Comparative Example 7, except that no pigment was contained in the first layer. That is, in Comparative Example 8, no pigment is contained in each of the first, second, and third layers 140, 150, 450.

Fusion-Bonding Result

As shown in Table 2, it was found that the first, second, and third layers 140, 150, 450 were satisfactorily fusion-bonded together in Examples 1, 2, 3, 4, 5, 6, and 7. In addition, it was also found that in Examples 1, 2, 3, 4, 5, 6, and 7, the second layer 150 did not undergo deformation (melting), which would cause leakage or a decrease in the sliding ability of the guide wire 200, because of the melting point of the second layer 150 greater (at least 10° C. greater) than that of the first layer 140.

Furthermore, it has been demonstrated that in Examples 1, 2, 3, 4, 5, 6, and 7, the third layer 450 can function as a buffer layer for reducing the heat transfer between the first and second layers 140, 150, so that the second layer 150 can be more advantageously prevented from being deformed. In addition, in Examples 1, 2, 3, 5, and 6, heat generating light is less absorbed into the third layer 450, which contains no pigment. Therefore, it has been demonstrated that in Examples 1, 2, 3, 5, and 6, the second layer 150 can be more advantageously prevented from being deformed than in Examples 4 and 7.

In Comparative Examples 1 and 2, no fusion-bonded portion was formed because of no pigment in each of the first, second, and third layers 140, 150, 450.

In Comparative Examples 3 and 4, the second layer 150 underwent deformation (melting), which would cause leakage or a decrease in the sliding ability of the guide wire 200. This may be because the melting point of the second and third layers 150, 450 is lower than that of the first layer 140. In addition, it was observed that in Comparative Example 3, the second layer 150, which contained the pigment, more significantly underwent deformation (melting).

In Comparative Example 5, the second layer 150 underwent deformation (melting), which would cause leakage or a decrease in the sliding ability of the guide wire 200, because the third layer 450 between the first and second layers 140, 150 contained the pigment. In Comparative Example 5, the melting point of the second layer 150 forming the inner peripheral surface of the inner tube shaft 130 is lower than that of the first layer 140 and is approximately equal to that of the third layer 450. Therefore, it is suggested that in Comparative Example 5, heat may be transferred from the third layer 450 to the second layer 150 to deform the second layer 150 when heat generating light is applied so that a fusion-bonded portion can be formed.

In Comparative Example 6, no fusion-bonded portion was formed because of no pigment in each of the first, second, and third layers 140, 150, 450.

In Comparative Example 7, the second layer 150 underwent deformation (melting), which would cause leakage or a decrease in the sliding ability of the guide wire 200. This may be because the melting point of the second layer 150 is lower than the melting point of the material of the first layer 140.

In Comparative Example 8, no fusion-bonded portion was formed because of no pigment in each of the first, second, and third layers 140, 150, 450.

TABLE 2

|  | Fusion-bonding Result |
| --- | --- |
| Example 1 | Excellent |
| Example 2 | Excellent |
| Example 3 | Excellent |
| Example 4 | Good |
| Example 5 | Excellent |
| Example 6 | Excellent |
| Example 7 | Good |
| Comparative Example 1 | Poor |
| Comparative Example 2 | Poor |
| Comparative Example 3 | Poor |
| Comparative Example 4 | Poor |
| Comparative Example 5 | Poor |
| Comparative Example 6 | Poor |
| Comparative Example 7 | Poor |
| Comparative Example 8 | Poor |

The results indicate that when the third layer 450 is provided between the first and second layers 140, 150 of the inner tube shaft 130, the second layer 150 can be more effectively prevented from undergoing deformation (melting), which would cause leakage or a decrease in the sliding ability of the guide wire 200.

While the balloon catheter and the method of manufacturing the balloon catheter according to the present disclosure have been described with reference to the embodiment, the scope of the present disclosure is not limited to the contents described in the embodiment, and may be appropriately modified based on the scope of the appended claims.

For example, a structure or a member arrangement of the balloon catheter described in the embodiment can be appropriately modified. Additional members described in the drawings may be appropriately omitted in use, or other additional members which are not particularly described may be appropriately used. Similarly, the respective steps or the tools used for the method of manufacturing the balloon catheter may be appropriately modified.

The detailed description above describes to a balloon catheter and a method of manufacturing a balloon catheter. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon catheter comprising:
an outer tubular shaft having a lumen;
an inner tubular shaft located in the lumen of the outer tubular shaft, the inner tubular shaft having a first layer and a second layer, the second layer being located on an inner surface side of the first layer;
the inner tubular shaft having a third layer interposed between the first layer and the second layer, and a material of the third layer having a greater affinity for a material of the second layer than the affinity of the material of the third layer for a material of the first layer;
a balloon fixed to a distal side of the inner tubular shaft and a distal side of the outer tubular shaft, and the outer tubular shaft being recessed toward the inner tubular shaft;
the material of the first layer having an optical absorption property greater than an optical absorption property of the material of the outer tubular shaft and an optical absorption property of the material of the second layer, and a melting point of the material of the second layer is greater than a melting point of the material of the first layer; and
wherein the material of the third layer has an optical absorption property lower than an optical absorption property of the material of the first layer.

2. The balloon catheter according to claim 1, wherein a thickness of the second layer is same as a thickness of the first layer in a cross section perpendicular to an axial direction of the inner tubular shaft.

3. The balloon catheter according to claim 1, wherein a thickness of the second layer is less than a thickness of the first layer in a cross section perpendicular to an axial direction of the inner tubular shaft.

4. The balloon catheter according to claim 1, wherein the melting point of the material of the second layer is at least 10 degrees greater than the melting point of the material of the first layer.

5. The balloon catheter according to claim 1, wherein the first layer is an outermost layer of the inner tubular shaft.

6. The balloon catheter according to claim 1, wherein in a cross section perpendicular to an axial direction of the inner tubular shaft, a thickness of the first layer increases toward a fusion-bonded portion between the outer tubular shaft and the inner tubular shaft.

7. The balloon catheter according to claim 1, wherein the outer tubular shaft is fusion-bonded to the first layer.

8. The balloon catheter according to claim 1, comprising:
a fusion-bonded portion in a portion of the outer tubular shaft fusion-bonded to the first layer of the inner tubular shaft in a state where the outer tubular shaft is recessed toward the inner tubular shaft.

9. The balloon catheter according to claim 8, wherein the fusion-bonded portion is located between 5 mm to 220 mm proximal to a proximal portion of the balloon.

10. A balloon catheter comprising:
an outer tubular shaft having a lumen;
an inner tubular shaft located in the lumen of the outer tubular shaft, the inner tubular shaft having a first layer, a second layer located on an inner surface side of the first layer, and a third layer interposed between the first layer and the second layer;
a balloon fixed to a distal side of the inner tubular shaft and a distal side of the outer tubular shaft, and the outer tubular shaft being recessed toward the inner tubular shaft;
a material of the first layer having an optical absorption property greater than an optical absorption property of a material of the outer tubular shaft and an optical absorption property of a material of the second layer, and a melting point of the material of the second layer is at least 10° C. greater than a melting point of the material of the first layer;
a material of the third layer has a greater affinity for the material of the second layer than the affinity of the material of the third layer for the material of the first layer; and
wherein the material of the third layer has an optical absorption property lower than an optical absorption property of the material of the first layer.

11. The balloon catheter according to claim 10, wherein a thickness of the second layer is same as a thickness of the first layer in a cross section perpendicular to an axial direction of the inner tubular shaft, or wherein the thickness of the second layer is less than the thickness of the first layer in the cross section perpendicular to the axial direction of the inner tubular shaft.

12. The balloon catheter according to claim 10, wherein the first layer is an outermost layer of the inner tubular shaft.

13. The balloon catheter according to claim 10, wherein in a cross section perpendicular to an axial direction of the inner tubular shaft, a thickness of the first layer increases toward a fusion-bonded portion between the outer tubular shaft and the inner tubular shaft.

14. The balloon catheter according to claim 10, wherein the outer tubular shaft is fusion-bonded to the first layer.

* * * * *